United States Patent [19]

Rottmaier et al.

[11] 4,419,520

[45] Dec. 6, 1983

[54] HYDROXYALKYL- AND ALKOXYALKYL-TRIAZOLIDINE-3,5-DIONE COMPOUNDS AND THEIR PROCESSES FOR THEIR PREPARATION

[75] Inventors: Ludwig Rottmaier, Odenthal; Ruldolf Merten, Leverkusen, both of Fed. Rep. of Germany

[73] Assignee: Bayer Aktiengesellschaft, Leverkusen, Fed. Rep. of Germany

[21] Appl. No.: 278,369

[22] Filed: Jun. 29, 1981

[30] Foreign Application Priority Data

Jul. 21, 1980 [DE] Fed. Rep. of Germany ....... 3027596

[51] Int. Cl.$^3$ .......................................... C07D 249/12
[52] U.S. Cl. .................................................... 548/264
[58] Field of Search ......................................... 548/264

[56] References Cited

FOREIGN PATENT DOCUMENTS

| 1104965 | 4/1961 | Fed. Rep. of Germany | ...... 548/264 |
| 2908627 | 9/1980 | Fed. Rep. of Germany | ...... 548/264 |
| 2156972 | 5/1973 | France | ............................ 548/264 |

OTHER PUBLICATIONS

Chem. Abs., vol. 80: 4880m–Index Page 39193cs of 9th Coll. Index (1978).

Primary Examiner—Mary C. Lee
Attorney, Agent, or Firm—Connolly and Hutz

[57] ABSTRACT

An hydroxyalkyl- and alkoxyalkyl-triazolidine-3,5-dione is disclosed of the formula

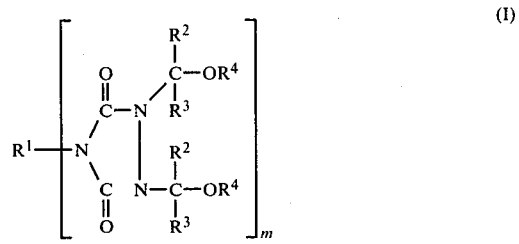

wherein $R^1$ represents an unsubstituted or substituted aliphatic radical, which is straight-chain or branched, with 1–20 C atoms, mono- or poly-cycloaliphatic radical with 5 to 21 C atoms, araliphatic radical with 7 to 17 C atoms or aromatic radical with 6 to 20 C atoms, each radical carrying m of the radicals shown in brackets, and it being possible for the aliphatic radicals to be interrupted by one or more oxygen atoms or tertiary nitrogen atoms and for the cycloaliphatic, araliphatic and aromatic radicals to be interrupted by one or more oxygen atoms, tertiary nitrogen atoms or methylene groups with 1 to 4 C atoms, $R^2$ and $R^3$ independently of one another denote hydrogen or a straight-chain or branched aliphatic radical with 1 to 10 C atoms, $R^4$ represents hydrogen or an aliphatic radical, which is straight-chain or branched, with 1 to 20 C atoms, mono- or poly-cycloaliphatic radical with 5 to 10 C atoms or araliphatic radical with 7 to 17 C atoms and m denotes an integer from 1 to 5, and wherein, in the case where m=1, $R^1$ can also represent the radical

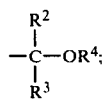

a process for the preparation of such compounds by reaction of a triazolidine-3,5-dione with an aliphatic aldehyde or ketone, optionally simultaneously with or followed by reaction of the resultant hydroxyalkyl triazolidine-3,5-diones with an alcohol.

20 Claims, No Drawings

HYDROXYALKYL- AND ALKOXYALKYL-TRIAZOLIDINE-3,5-DIONE COMPOUNDS AND THEIR PROCESSES FOR THEIR PREPARATION

The present invention relates to new hydroxyalkyl- and alkoxyalkyl-triazolidine-3,5-diones and processes for their preparation.

Hydroxyalkyl- and alkoxyalkyl-triazolidine-3,5-diones of the formula

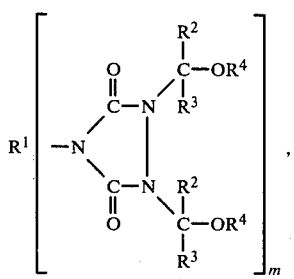

(I)

wherein $R^1$ represents an unsubstituted or substituted aliphatic radical, which is straight-chain or branched, with 1–20 C atoms, mono- or poly-cycloaliphatic radical with 5 to 21 C atoms, araliphatic radical with 7 to 17 C atoms or aromatic radical with 6 to 20 C atoms, each radical carrying m of the radicals shown in brackets, and it being possible for the aliphatic radicals to be interrupted by one or more oxygen atoms or tertiary nitrogen atoms and for the cycloaliphatic, araliphatic and aromatic radicals to be interrupted by one or more oxygen atoms, tertiary nitrogen atoms or methylene groups with 1 to 4 C atoms, $R^2$ and $R^3$ independently of one another denote hydrogen or a straight-chain or branched aliphatic radical with 1 to 10 C atoms, $R^4$ represents hydrogen or an aliphatic radical, which is straight-chain or branched, with 1 to 20 C atoms, mono- or poly-cycloaliphatic radical with 5 to 10 C atoms or araliphatic radical with 7 to 17 C atoms and m denotes an integer from 1 to 5, and wherein, in the case where m=1, $R^1$ can also represent the radical

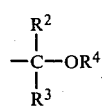

have been found.

Aliphatic radicals $R^1$ which may be mentioned are preferably radicals with 1 to 12 C atoms and particularly preferably radicals with 1 to 9 C atoms. These radicals can be alkyl, alkenyl, alkynyl.

Cycloaliphatic radicals $R^1$ which may be mentioned are preferably radicals with 6 to 10 C atoms. Particularly contemplated are cycloalkyl radicals.

Araliphatic radicals $R^1$ which may be mentioned are preferably radicals with 7 to 10 C atoms. Particularly contemplated are aryl radicals which have an alkyl substituent as the aliphatic component.

Aromatic radicals $R^1$ which may be mentioned are preferably radicals with 6 to 14 C atoms and particularly preferably radicals with 6 to 10 C atoms.

Substituents of $R^1$ which may be mentioned are halogen, such as fluorine, chlorine and bromine, and also $C_1$-$C_{10}$-alkoxy and -alkoxycarbonyl. Chlorine and $C_1$-$C_4$-alkoxy may be mentioned as preferred.

Aliphatic radicals $R^2$ and $R^3$ which may be mentioned are preferably those with 1 to 4 C atoms, such as alkyl radicals, for example methyl, ethyl, propyl and butyl. $R^2$ and $R^3$ are particularly preferably hydrogen.

Aliphatic radicals $R^4$ which may be mentioned are preferably those with 1 to 12 C atoms, cycloaliphatic radicals $R^4$ which may be mentioned are those with 5 to 10 C atoms, especially cycloalkyl, and araliphatic radicals $R^4$ which may be mentioned are those with 7 to 10 C atoms, especially aralkyl radicals. $R^4$ is particularly preferably hydrogen or, in the case of an aliphatic radical, one with 1 to 4 C atoms, e.g. alkyl, such as methyl, ethyl, propyl or butyl, or the benzyl radical.

m preferably represents the number 1, 2 or 3, and particularly preferably the number 1 or 2.

Compounds of the formula

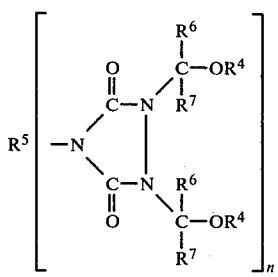

(Ia)

wherein $R^4$ has the meaning given, $R^5$ has the meaning given for $R^1$, $R^6$ and $R^7$ simultaneously or independently of one another represent hydrogen or methyl and n denotes the number 1, 2 or 3, and wherein, in the case where n=1, $R^5$ can also represent the radical

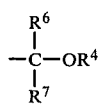

may be mentioned as preferred compounds according to the invention.

Compounds of the formula

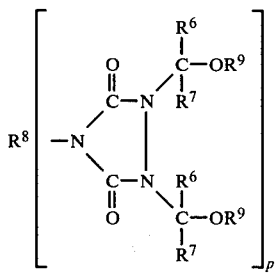

(Ib)

wherein $R^6$ and $R^7$ have the meaning given, $R^8$ has the meaning given for $R^1$, $R^9$ represents hydrogen or an alkyl radical which is straight-chain or branched, with 1 to 12 C atoms, a cycloalkyl radical with 5 or 6 C atoms or an araliphatic radical with 7 to 17 C atoms, especially an aralkyl radical, and p denotes the number 1, 2 or 3, and wherein, in the case where p=1, $R^8$ can also represent the radical

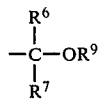

may also be mentioned as preferred.

Compounds of the formula

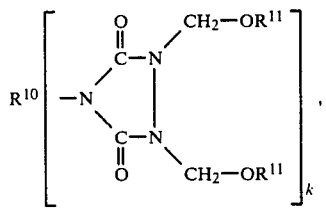   (Ic)

wherein $R^{10}$ has the meaning given for $R^1$, $R^{11}$ represents hydrogen, an alkyl radical with 1 to 4 C atoms, such as methyl, ethyl, propyl, isopropyl, butyl or isobutyl, the cyclohexyl radical or the benzyl radical and k represents the number 1, 2 or 3, and wherein, in the case where k=1, $R^{10}$ can also represent the radical

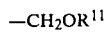

are particularly preferred.

Compounds of the formula

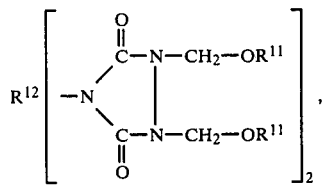   (Id)

wherein $R^{11}$ has the meaning given and $R^{12}$ represents

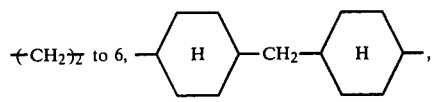

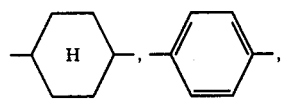

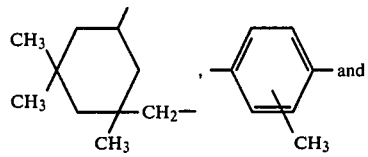

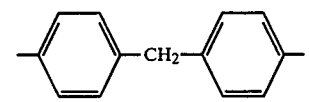

are also particularly preferred.

Furthermore, a process has been found for the preparation of hydroxyalkyl- and alkoxyalkyl-triazolidine-3,5-diones of the formula

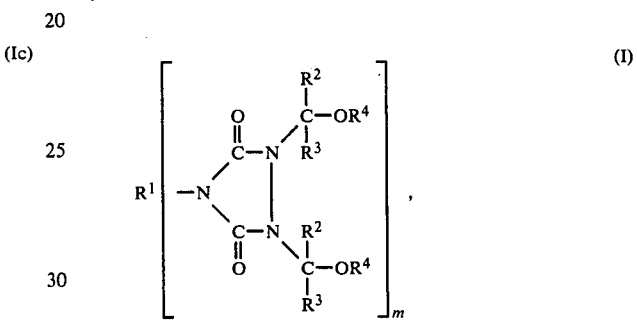   (I)

wherein $R^1$ represents an unsubstituted or substituted aliphatic radical, which is straight-chain or branched, with 1–20 C atoms, mono- or poly-cycloaliphatic radical, with 5 to 21 C atoms, araliphatic radical with 7 to 17 C atoms or aromatic radical with 6 to 20 C atoms, each radical carrying m of the radicals shown in brackets, and it being possible for the aliphatic radicals to be interrupted by one or more oxygen atoms or tertiary nitrogen atoms and for the cycloaliphatic, araliphatic and aromatic radicals to be interrupted by one or more oxygen atoms, tertiary nitrogen atoms or methylene groups with 1 to 4 C atoms, $R^2$ and $R^3$ independently of one another denote hydrogen or a straight-chain or branched aliphatic radical with 1 to 10 C atoms, $R^4$ represents hydrogen or an aliphatic radical, which is straight-chain or branched, with 1 to 20 C atoms, mono- or poly-cycloaliphatic radical with 5 to 10 C atoms or araliphatic radical with 7 to 17 C atoms and m denotes an integer from 1 to 5, and wherein, in the case where m=1, $R^1$ can also represent the radical

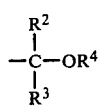

which is characterised in that a triazolidine-3,5-dione of the formula

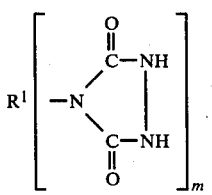

(II)

wherein

R$^{1'}$ represents an unsubstituted or substituted aliphatic radical, which is straight-chain or branched with 1 to 20 C atoms, mono- or poly-cycloaliphatic radical, with 5 to 21 C atoms, araliphatic radical with 7 to 17 C atoms or aromatic radical with 6 to 20 C atoms, each radical carrying m of the radicals shown in brackets, and it being possible for the aliphatic radicals to be interrupted by one or more oxygen atoms or tertiary nitrogen atoms and for the cycloaliphatic, araliphatic and aromatic radicals to be interrupted by one or more oxygen atoms, tertiary nitrogen atoms or methylene groups with 1 to 4 C atoms, m denotes an integer from 1 to 5, and wherein, in the case where m=1, R$^1$ can also represent the radical hydrogen, are reacted with aliphatic aldehydes or ketones of the formula

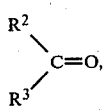

(III)

wherein R$^2$ and R$^3$ have the meaning given, if desired in the presence of a catalyst, and, if desired, the resulting hydroxyalkyltriazolidine-3,5-dione of the formula (I) in which R$^4$ denotes H is reacted with an alcohol of the formula

R$^4$OH     (IV)

wherein R$^4$ has the meaning given, if desired in the presence of a catalyst.

In the process according to the invention, it is thus possible to react triazolidine-3,5-diones of the formula (II) with aldehydes or ketones of the formula (III) to give hydroxyalkyltriazolidine-3,5-diones of the formula (V), which corresponds to the formula (I) with R$^4$ denoting H.

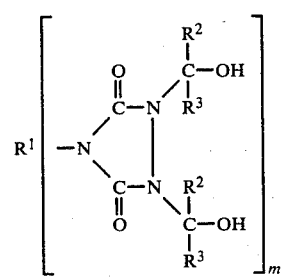

(V)

In this formula, R$^1$, R$^2$ and R$^3$ and m have the meaning given.

These compounds can be isolated and converted into the alkoxyalkyl-triazolidine-3,5-diones of the formula (I) in a further reaction with alcohols of the formula (IV).

However, it is also possible for the hydroxyalkyltriazolidine-3,5-diones of the formula (V) to be reacted with alcohols of the formula (IV) in a subsequent reaction step, without being isolated, to give the alkoxyalkyl-triazolidine-3,5-diones of the formula (I).

The process according to the invention can, however, also be carried out by a procedure in which triazolidine-3,5-diones of the formula (II) are reacted simultaneously with aldehydes or ketones of the formula (III) and alcohols of the formula (IV). Alkoxyalkyltriazolidine-3,5-diones of the formula (I) can be isolated in this case.

The process according to the invention is preferably carried out by a procedure in which the hydroxyalkyltriazolidine-3,5-diones of the formula (V) are prepared and, if desired, are reacted with alcohols of the formula (IV).

Triazolidine-3,5-diones of the formula (II) in which m=1 can be used for the preparation of the new hydroxyalkyl- and alkoxyalkyl-triazolidine-3,5-diones of the formula (I). These diones of the formula (II) are known, and they can be prepared by reaction of hydrazinocarboxylates with monoisocyanates and subsequent cyclization of the products, or from hydrazine-N,N'-dicarboxylic acid diamide by heating to 200° C. (Liebigs Annalen der Chemie, volume 238, page 41 (1894)).

Triazolidine-3,5-diones of the formula (II) which carry several of the radical in brackets (m greater than 1) can be obtained by a process in which amines of the formula R$^1$(NH$_2$)$_m$     (VI)

wherein R$^1$ and m have the meaning given, are reacted with hydrazodicarboxamide or with 1,2,4-triazolidine-3,5-dione at 150°–280° C. in the presence or absence of a solvent, such as N-methylpyrrolidone, or of a solvent mixture under pressures from 50 mbars to 5 bars, if appropriate in the presence of an acid or basic catalyst, such as an alcoholate or a tertiary amine, ammonia being split off.

Triazolidine-3,5-diones of the formula (II) which contain several of the radical in brackets (m greater than 1) can also be obtained when hydrazodicarboxamides of the formula

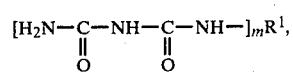     (VII)

wherein R$^1$ and m have the meaning given, are cyclized under the abovementioned conditions, ammonia being split off.

N-Monosubstituted hydrazodicarboxamides of the formula (VII) can be obtained by processes analogous to known processes from semicarbazide and isocyanates of the formula (VIII)

R$^1$(NCO)$_m$     (VIII)

wherein R$^1$ and m have the meaning given, (Saunder and Frisch, "Polyurethanes" Part I, page 205, Interscience Publishers 1962).

Aliphatic aldehydes or ketones can be used as the aldehydes or ketones of the formula (III) to be employed according to the invention. Examples which may be mentioned are: formaldehyde, acetaldehyde, propionaldehyde, butyraldehyde, 2-ethylheptanal, acetone, butanone, methyl isopropyl ketone, methyl isobutyl ketone, dipropyl ketone, 3-methyl-5-heptanone and dinonyl ketone. Formaldehyde, either in gaseous form or in aqueous solution, or in polymeric form, is preferably used. It is also possible to use mixtures of the oxo compounds to be employed according to the invention.

Acid, basic or neutral catalysts can be used in the reaction of the triazolidine-3,5-diones of the formula (II) with aldehydes or ketones of the formula (III). Basic catalysts, such as tertiary amines or quaternary ammonium salts, such as triethylamine, tri-n-butylamine, triethanolamine, N,N'-dimethylaniline, urotropine and tetramethylammonium chloride, alkali metal hydroxides and alkaline earth metal hydroxides, such as sodium hydroxide and barium hydroxide, and basic alkali metal salts and alkaline earth metal salts, such as sodium tetraborate, lithium carbonate and barium carbonate, are preferably employed. The amount of catalyst is between 0.001 and 10%, relative to the weight of the reactants.

In principle, the reaction of the triazolidine-3,5-dione with aldehydes or ketones can also be carried out without the addition of catalysts, but higher temperatures and/or longer reaction times may then become necessary.

The reaction of the triazolidine-3,5-diones of the formula (II) with aldehydes and ketones of the formula (III) can be carried out using stoichiometric amounts of aldehydes and ketones, that is to say 1 mol of aldehyde or ketone is employed per NH group which can be occupied. It is also possible to employ an excess of aldehyde or ketone. Stoichiometric amounts are preferably used.

However, it is also possible to employ less than 1 mol of aldehyde or ketone per NH group which can be occupied, so that products with free NH groups can be formed. When these products are incorporated into polymers, the free NH groups can further react by known reactions, so that quite specific modified plastics may be obtained.

Solvents can be used in the reaction of the triazolidine-3,5-diones of the formula (II) with aldehydes or ketones of the formula (III); the aldehyde or ketone (III) can also serve as the solvent. Solvents used are polar, optionally water-miscible organic solvents. Water, alcohols, such as methanol, ethanol, n-propanol, i-propanol, n-butanol and i-butanols dimethylformamide, dimethylacetamide, N-methylpyrrolidone, dimethyl sulphone and sulpholane may be mentioned as preferred.

The reaction between the triazolidine-3,5-diones of the formula (II) and the aldehydes or ketones of the formula (III) is carried out at 10° to 200° C., preferably at 20° to 150° C., and if appropriate under increased pressure.

The reaction times can vary greatly. They can be between, for example, 30 minutes and several days. The reaction times can be shortened by appropriate choice of the reaction conditions, for example by an increase in temperature and any increase in pressure which may thereby be necessary, or only by an increase in pressure.

Aliphatic, cycloaliphatic and araliphatic alcohols are used as the alcohols of the formula (IV) to be employed according to the invention. Examples which may be listed are: methanol, ethanol, iso- and n-propanol, n-butanol, isobutanol, amyl alcohol, 1-octanol, 1-decanol, 1-dodecanol, stearyl alcohol, allyl alcohol, glycol monomethyl ether, cyclohexanol and benzyl alcohol. Methanol, ethanol, isopropanol, butanol, cyclohexanol and benzyl alcohol are particularly preferably employed. It is, of course, also possible to use mixtures of the alcohols to be employed according to the invention.

Acid, basic or neutral catalysts can be used in the reaction of the hydroxyalkyl-triazolidine-3,5-diones of the formula (V) with alcohols of the formula (IV). Acid catalysts are preferably employed. Particularly preferred catalysts are mineral acids, such as hydrochloric acid and sulphuric acid, organic acids, such as oxalic acid, acetic acid, formic acid and benzoic acid, and Lewis acids, such as boron trifluoride, aluminum fluoride and zinc-II chloride. Organometallic compounds, such as titanium tetrabutylate and zinc octoate, may also be mentioned. The catalysts can be used in amount between 0.001 and 1% by weight.

In principle, the reaction of the hydroxyalkyl-triazolidine-3,5-diones with the alcohols can also be carried out without the addition of catalysts, but higher temperatures and/or longer reaction times may then become necessary.

The reaction of the hydroxyalkyl-triazolidine-3,5-diones of the formula (V) with alcohols of the formula (IV) can be carried out using stoichiometric amounts of alcohol, that is to say 1 mol of alcohol per etherifiable hydroxyl group. It is also possible to employ an excess of alcohol. If an excess of alcohol is used, this is kept as low as possible, especially in the case of high-boiling alcohols.

It is also possible to employ less than 1 mol of alcohol per etherifiable hydroxyalkyl group, so that products with free hydroxyl groups are formed. Such hydroxyalkyl- and alkoxyalkyl-triazolidine-3,5-diones containing hydroxyl groups can also be formed when the reaction between the hydroxyalkyl-triazolidine-3,5-diones and alcohols is interrupted prematurely. When these products are incorporated into polymers, the free hydroxyl groups can further react by known reactions, so that specific, modified plastics can be obtained.

If water-immiscible alcohols are used, the excess alcohol can serve as an entraining agent for the water formed during the reaction. However, it is, of course, also possible for other water-immiscible solvents to serve as entraining agents for azeotropic removal, by distillation, of the water formed during the reaction.

Aliphatic, araliphatic and aromatic hydrocarbons and industrial mixtures an halogenation products thereof are used, in particular, as the entraining agent. Examples which may be mentioned are: hexane, octane, cyclohexane, toluene, xylene, methylene chloride, chloroform, dichloroethane and chlorobenzene.

The reaction between the hydroxyalkyl-triazolidine-3,5-diones and the alcohols is in general carried out at 30°–200° C., preferably at 50°–150° C., if appropriate under increased pressure.

The reaction times can vary greatly. They can be between, for example, from one hour up to several days. The reaction times can be shortened by appropriate choice of the reaction conditions, for example by an increase in temperature and by any increase in pressure which may thereby be necessary, or only by increasing the pressure.

The alkoxyalkyl-triazolidine-3,5-diones of the formula (I) are valuable starting materials for the preparation of polymeric compounds. They can be employed for the preparation and modification of phenolic resins, urea resins and melamine resins. The alkoxyalkyltriazolidine-3,5-diones according to the invention can be mixed with phenol- or urea- or melamine-formaldehyde resins, for example a novolak resin of phenol and formaldehyde and optionally with a catalyst, in particular with an acid catalyst such as, for example, oxalic acid, and can be processed into hard transparent moulded articles by being heated. Using pressure, pressed articles, for example chipboard sheets can be produced from such mixtures with the addition of fillers, for example, sawdust, and optionally other additives such as, for example flameproofing agents.

In addition, these alkoxyalkyl-triazolidine-3,5-diones according to the invention, can be used for the production of stoving lacquers. For this purpose the alkoxyalkyl-triazolidine-3,5-diones are mixed or dissolved, optionally in a solvent such as for example glycolmonomethyl ether acetate, with hydroxyl-group-containing polymers such as hydroxyl-group containing polyesters of, for example, terephthalic acid, phthalic acid, adipic acid, glycol, diglycol, glycerol or polyethers, such as for example, those obtained from biphenoles and alkylene oxides, and after the addition of a suitable acid catalyst, for example p-toluenesulphonic acid, are stoved into smooth and elastic lacquers.

The examples which follow are intended to illustrate the invention in more detail. In the examples, unless otherwise indicated, the percentages denote percentages by weight and the parts denote parts by weight.

EXAMPLES

EXAMPLE 1

Preparation of the starting 1,2,4-triazolidine-3,5-diones:

(a) Preparation of 1,2,4-triazolidine-3,5-dione 3 kg of sulpholane and 1.18 kg of hydrazodicarboxamide which have been dried in air are heated to 200° C., in the course of 2.5 hours, in a 6 l three-necked flask equipped with a stirrer, thermometer, dropping funnel and distillation bridge, a slight vacuum being applied at the start of the evolution of ammonia at 150°–160° C. The temperature is then increased to 210° C. in the course of one hour. After about 1.5 hours, a clear solution is formed, and stirring is continued for about a further 3.5 hours at 210° C. and under 200 mbars until the reaction has ended. After cooling the mixture to 180° C., the residual ammonia is removed under 40 to 80 mbars. 0.8 kg of toluene are added dropwise to the cooling solution under normal pressure in a manner such that virtually no toluene is distilled off. The almost pure 1,2,4-triazolidine-3,5-dione which has crystallised out is filtered off, after cooling the mixture to room temperature, and washed with toluene. 0.87 kg (=86.2% of theory) of dried 1,2,4-triazolidine-3,5-dione with a purity of 97.5%, determined by titration with N/10 sodium hydroxide solution using phenolphthalein, is obtained.

(b) Preparation of 1,2-ethanediyl-4,4'-bis-1,2,4-triazolidine-3,5-dione 600 g of hydrazodicarboxamide and 150 g of ethylenediamine in 500 ml of N-methylpyrrolidone are stirred at 175° C. for 4 hours and at 200° C. for 20 hours. When the mixture cools, a precipitate separates out and is filtered off and washed with ethanol. 462 g (80% of theory) of 1,2-ethanediyl-4,4'-bis-1,2,4-triazolidine-3,5-dione are obtained as colourless crystals of melting point >330° C.

(c) Preparation of 4,4'-bis-(1,2,4-triazolidine-3,5-dion-4-yl)-dicyclohexylmethane 420 g of 4,4'-diaminodicyclohexylmethane and 472 g of hydrazodicarboxamide in 750 ml of N-methylpyrrolidone are stirred at 175° C. for 4 hours, at 200° C. for 8 hours and at 220° C. for 4 hours. The reaction product is cooled and then stirred into 3 l of water. A precipitate thereby separates out and is filtered off and washed with water. 566 g (75% of theory) of 4,4'-bis-(1,2,4-triazolidine-3,5-dion-4-yl)-dicyclohexylmethane are obtained as colourless crystals of melting point 305° C. (decomposition).

(d) Preparation of 4-phenyl-1,2,4-triazolidine-3,5-dione

Sodium carbonate is added in small portions to a solution of 111.5 g of semicarbazide hydrochloride in 700 g of water until no further evolution of gas can be observed.

A solution of 119 g of phenyl isocyanate in 100 g of acetone is then added dropwise at 40° C. The mixture is subsequently stirred at 40° C. for 2 hours in order to bring the reaction to completion, and the precipitate formed is isolated by filtration.

The precipitate is dried in air overnight and is suspended in 300 g of sulpholane, and the suspension is heated to 205° C., the ammonia liberated being stripped off from 160° C. by applying a waterpump vacuum of 420 mbars. After a reaction time of 5 hours, most of the solvent is removed under a pressure of 0.3 mbar and the residue which remains is recrystallised from n-butanol. After filtering off and drying, 134 g of 4-phenyl-1,2,4-triazolidine-3,5-dione of melting point 202°–203° C. (literature: 203° C.) are obtained.

EXAMPLE 2

505 g of triazolidine-3,5-dione are added, whilst stirring, to 1,220 g of 37% strength aqueous formaldehyde solution, to which 5 g of sodium hydroxide have been added, and the mixture is warmed to 80° C. Stirring is continued at 80° C. for one hour in order to bring the reaction to completion. The water present is distilled off from the clear solution by applying a vacuum, during which the temperature is not increased above 50° C. 945 g of tris-hydroxymethyl-triazolidine-3,5-dione containing 0.5% of water (determined by titration by the method of Fischer) and 45.71% of formaldehyde which can be split off (determined after acid distillation) are obtained. The IR spectrum and NMR spectrum and the elementary analysis confirm the assumed structure.

Calculated for $C_5H_9N_3O_5$: C=31.4%; H=4.71%; N=22.0%; OH=25.7%; Found: C=31.2%; H=4.9%; N=22.1%; OH=24.6%.

EXAMPLE 3

50.5 g of triazolidine-3,5-dione in 122 g of 37% strength aqueous formaldehyde solution, to which 0.5 g of borax has been added, are warmed to 80° C. and the mixture is stirred at 80° C. for one hour. The water is distilled off in vacuo, under 30 mbars and at temperatures which do not exceed 50° C. 98.5 g of tris-hydroxymethyl-triazolidine-3,5-dione containing 4.8% of water and 42.83% of formaldehyde which can be split off are obtained.

EXAMPLE 4

95.5 g of the tris-hydroxymethyl-triazolidine-3,5-dione prepared according to Example 1 are dissolved in 300 g of n-butanol, and concentrated sulphuric acid is added until a pH of 2 is reached. This solution is heated under reflux for 2.5 hours, during which the water liberated is removed via a water separator. After cooling the mixture, a little insoluble residue is removed by filtration and the resulting solution is freed from volatile constituents at 60° C. in vacuo, the final pressure being 0.3 mbar. 169 g of crude tris-butoxymethyl-triazolidine-3,5-dione are obtained. For purification, the product is dissolved in ethyl acetate and this solution is extracted by shaking with dilute sodium hydroxide solution and then with water. After distilling off the solvent, 151 g of virtually pure tris-butoxymethyl-triazolidine-3,5-dione, the structure of which is proved by the IR spectrum and NMR spectrum and by elementary analysis, are obtained.

Calculated for $C_{17}H_{33}N_3O_5$: C=57.7%; H=9.18%; N=11.2%; Found: C=57.9%; H=9.4%; N=11.1%.

EXAMPLE 5

95.5 g of the tris-hydroxymethyl-triazolidine-3,5-dione prepared according to Example 1, 162 g of benzyl alcohol and 250 ml of toluene are adjusted to pH 2 with concentrated sulphuric acid and the mixture is heated under reflux for 2.5 hours, during which the water liberated is removed via a water separator. The cooled solution is freed from a little insoluble residue by filtration and is concentrated in vacuo. After drying the residue at an oil bath temperature of 130° C. under 0.3 mbar, 182 g of an oily, light-yellow liquid remain. For purification, the product is dissolved in ethyl acetate and the solution is extracted by shaking with 5% strength sodium hydroxide solution and then with water. The solvent is removed in a rotary evaporator, whereupon 176 g of virtually pure tris-benzoxymethyl-triazolidine-3,5-dione, the structure of which is proved by means of the IR spectrum and NMR spectrum and by elementary analysis, are obtained.

Calculated for $C_{26}H_{27}N_3O_5$: C=67.7%; H=5.85%; N=9.12%; Found: C=68.0%; H=6.1%; N=9.1%.

EXAMPLE 6

4 g of p-toluenesulphonic acid are added to a solution of 191 g of the tris-hydroxymethyl-triazolidine-3,5-dione from Example 1 in 500 ml of ethanol, and the mixture is stirred under reflux for 12 hours. The volatile constituents are removed at 60° C. in vacuo, the final pressure being 0.3 mbar. 256 g of crude tris-ethoxymethyl-triazolidine-3,5-dione are thus obtained. For purification, the product is dissolved in ethyl acetate and the solution is washed with 5% strength sodium hydroxide solution and then with water. After removing the solvent in a rotary evaporator, 173 g of virtually pure tris-ethoxymethyl-triazolidine-3,5-dione, the structure of which is proved by the IR spectrum and NMR spectrum and by elementary analysis, remain.

Calculated for $C_{11}H_{21}N_3O_5$: C=48.0%; H=7.63%; N=15.27%; Found: C=47.8%; H=7.5%; N=15.4%.

EXAMPLE 7

50.5 g of triazolidine-3,5-dione are added to 122 g of 37% strength aqueous formalin solution, which contains 0.5 g of sodium tetraborate, and the mixture is stirred at 80° C. for one hour. Most of the water is removed by applying a vacuum at temperatures of up to 50° C. The viscous residue is dissolved in 300 ml of methanol and the solution is dried with anhydrous sodium sulphate. 2 g of p-toluenesulphonic acid are added to the anhydrous, methanolic solution and the mixture is stirred under reflux. After boiling the mixture for 5 hours, the reaction is interrupted and the solvent is removed in vacuo, the final pressure being 0.3 mbar, at temperatures of up to 45° C. 103 g of a yellowish, viscous residue which, according to the IR spectrum, still contains hydroxyl groups are obtained. Analysis of the hydroxyl groups shows 7.9% of OH groups, so that about ⅔ of the hydroxymethyl groups have reacted to give methoxymethyl groups. The NMR spectrum also proved that about ⅔ of the groups formed were methoxymethyl groups and about ⅓ were hydroxymethyl groups.

EXAMPLE 8

1,515 g of triazolidine-3,5-dione are added in portions to 3,900 g of 37% strength aqueous formaldehyde solution, which contains 15 g of NaOH, at room temperature, whilst stirring. The solution formed is stirred at 50° C. for one hour, and most of the water is removed by applying a waterpump vacuum. The light-yellow viscous residue formed is crystallised by dissolving in acetone and subsequently cooling the solution. After filtering off and drying the precipitate, 2,091 g (=72.7% of theory) of pure tris-hydroxymethyl-triazolidine-3,5-dione (melting point=109°-110° C.), the structure of which is proved by means of the IR spectrum and NMR spectrum and elementary analysis, are obtained.

Calculated for $C_5H_9N_3O_5$: C=31.4%; H=4.71%; N=22.0%; Found: C=31.5%; H=4.7%; N=21.9%.

EXAMPLE 9

13.3 g of paraformaldehyde are dissolved in a solution of 0.7 g of NaOH in 50 g of methanol at room temperature. 22.8 g of 1,2-bis-(triazolidine-3,5-dion-4-yl)-ethane are stirred into the resulting clear solution at room temperature and, when the slightly exothermic reaction has ended, the mixture is stirred at 30° C. for 1 hour. The next day, the voluminous precipitate is filtered off and dried. 28 g of virtually pure tetramethylol-bis-triazolidine-3,5-dione (melting point=165°-167° C., measured on a Kofler bench), the structure of which is proved by the IR spectrum and NMR spectrum and by elementary analysis, are obtained.

Calculated for $C_{10}H_{16}N_6O_8$: C=34.5%; H=4.6%; N=24.1%; Found: C=34.4%; H=4.6%; N=24.2%.

EXAMPLE 10

A mixture of 660 g of n-butanol, 130 g of paraformaldehyde and 2.5 g of urotropine is heated under reflux until a clear solution is formed. After cooling the solution to room temperature, 378 g of 4,4'-bis-(triazolidine-3,5-dion-4-yl)-dicyclohexylmethane are added. This suspension is heated to 100° C. in the course of 30 minutes, 1 g of p-toluene-sulphonic acid is then added and the mixture is kept under azeotropic reflux for 6 hours, during which the water formed is removed via a water separator.

The cooled solution is diluted with ethyl acetate, washed with 5% strength sodium hydroxide solution and then with water, dried over sodium sulphate and concentrated in vacuo, the final pressure being 0.5 mbar and the final temperature being 50° C. 718 g of crude 4,4'-bis-[bis-(butoxymethyl)-triazolidine-3,5-dion-4-yl]- dicyclohexylmethane, the structure of which is proved by means of the IR spectrum and NMR spectrum and elementary analysis, are obtained.

Calculated for $C_{37}H_{66}N_6O_8$: C=61.5%; H=9.1%; N=11.6%; Found: C=61.1%; H=8.9%; N=11.9%.

EXAMPLE 11

(a) 93.2 g of 1,2-ethanediyl-4,4'-bis-1,2,4-triazolidine-3,5-dione are added to 150 g of 37% strength aqueous formaldehyde solution, which contains 0.5 g of 45% strength sodium hydroxide solution, at room temperature, whilst stirring. Thereafter, the temperature increases to 45° C. The clear solution is stirred at 50° C. for one hour and is concentrated by applying a vacuum. 250 g of n-butanol and 2.5 g of concentrated hydrochloric acid are added to the viscous residue and the mixture is warmed slowly until the butanol refluxes. The water still present and the water formed during the reaction is removed via a water separator. When the reaction has ended, a little insoluble residue is filtered off and the solution is diluted with 80 g of ethyl acetate and washed twice with water. The organic phase is dried over sodium sulphate and concentrated to constant weight in vacuo, the final pressure being 0.4 mbar and the final temperature being 60° C. A viscous, light-yellow oil which, according to the IR and NMR spectra and elementary analysis, consists chiefly of 1,2-ethanediyl-4,4'-bis-[bis-(n-butoxymethyl)-1,2,4-triazolidine-3,5-dione] is obtained.

Calculated for $C_{26}H_{48}N_6O_8$: C=54.6%; H=8.39%; N=14.7%; Found: C=54.4%; H=8.8%; N=15.1%.

(b) 32.1 g of a polyester which has 5.3% of hydroxyl groups and is prepared by esterification of terephthalic acid, ethylene glycol and glycerol, are dissolved in 32.1 g of ethylene glycol monomethyl ether-acetate, and 14.3 g of the resin prepared according to Example 11a and 0.46 g of p-toluenesulphonic acid are added and the components are mixed.

A sheet of iron coated with this solution is warmed at 160° C. for 20 minutes. An almost colourless lacquer film which has a glossy surface and a very good elasticity and does not break even when the iron sheet is folded results.

EXAMPLE 12

35.4 g of 4-phenyl-triazolidine-3,5-dione are stirred into 32.5 g of 37% strength formaldehyde solution, which has been adjusted to pH 9 with sodium hydroxide solution, at room temperature and the mixture is stirred at 60° C. for one hour. After distilling off the water in vacuo, 200 g of n-butanol and 0.5 g of concentrated sulphuric acid are added and the mixture is stirred under azeotropic reflux, using a water separator, until no water distils off. 50 g of ethyl acetate are added to the resulting solution and the mixture is extracted twice by shaking with water and, after drying over sodium sulphate, is concentrated in vacuo, the final pressure being 0.4 mbar and the final temperature being 60° C. 67 g of a viscous oil which, according to the IR and NMR spectra and elementary analysis, consists chiefly of 1,2-bis-(n-butoxymethyl)-4-phenyl-triazolidine-3,5-dione are obtained.

Calculated for $C_{18}H_{27}N_3O_4$: C=61.8%; H=7.74%; N=12.03%; Found: C=61.6%; H=7.6%; N=12.2%.

What is claimed is:

1. A compound of the formula

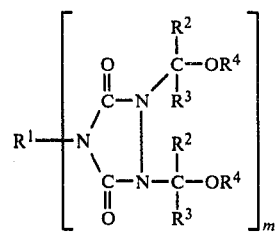

wherein m is an integer of from 1 to 5;

$R^1$ is an aliphatic group having 1 to 20 carbon atoms; a mono- or poly-cycloaliphatic group having from 5 to 21 carbon atoms; an araliphatic group having 7 to 17 carbon atoms; an aromatic group having 6 to 20 carbon atoms; one of the aforesaid groups substituted by halogen, $C_1$-$C_{10}$-alkoxy or $C_1$-$C_{10}$-alkoxycarbonyl;

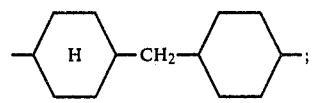

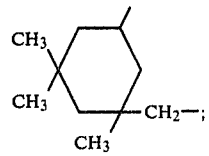

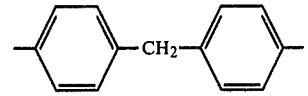

or, in the case where m is 1, $R^1$ can also be

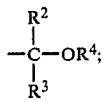

$R^2$ and $R^3$, independently of each other, are each hydrogen or an aliphatic group having 1 to 10 carbon atoms, and $R^4$ is hydrogen, an aliphatic group having 1 to 20 carbon atoms or a mono- or polycycloaliphatic group having 5 to 10 carbon atoms or an araliphatic group having 7 to 17 carbon atoms.

2. A compound of claim 1 wherein m is 1, 2 or 3;

$R^1$ is as aforesaid;

$R^2$ and $R^3$, independently of each other, are each hydrogen or methyl and $R^4$ is as aforesaid.

3. A compound of claim 1, wherein m is 1, 2 or 3;

$R^1$ is as aforesaid:

$R^2$ and $R^3$, independently of each other, are each hydrogen or methyl and $R^4$ is hydrogen, alkyl having 1 to 12 carbon atoms, cycloalkyl having 5 or 6 carbon atoms or an araliphatic radical having 7 to 17 carbon atoms.

4. A compound of claim 1 wherein m is 1, 2 or 3;

$R^1$ is as aforesaid;

$R^2$ and $R^3$ are each hydrogen, and $R^4$ is hydrogen, alkyl having 1 to 4 carbon atoms, cyclohexyl or benzyl.

5. A compound of claim 4 wherein m is 2 and $R^1$ is alkylene having 2 to 6 carbon atoms,

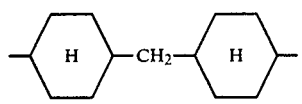

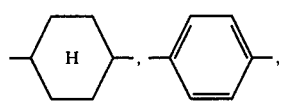

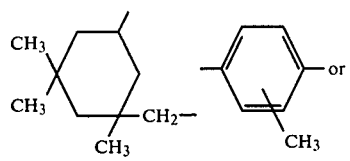

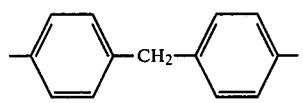

6. A compound according to claim 1, which is tris-butoxymethyl-triazolidine-3,5-dione.

7. A compound according to claim 1, which is tris-benzoxymethyl-triazolidine-3,5-dione.

8. A compound according to claim 1, which is tris-ethoxymethyl-triazolidine-3,5-dione.

9. A compound according to claim 1, which is tris-hydroxy-methyltriazolidine-3,5-dione.

10. A process for preparing a compound of claim 1 which comprises contacting a triazolidine-3,5-dione of the formula

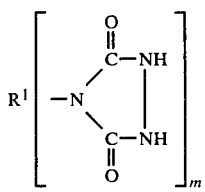

wherein m and $R^1$ are as aforesaid with an aliphatic aldehyde or ketone of the formula

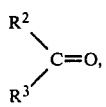

wherein $R^2$ and $R^3$ are as aforesaid and, when $R^4$ is to be other than hydrogen, reacting the resulting hydroxylalkyl triazolidine-3,5-dione with a compound of the formula $R^4OH$ wherein $R^4$ is as aforesaid.

11. A process according to claim 10, wherein the reaction of triazolidine-3,5-dione with aliphatic aldehyde or ketone is effected in the presence of a catalyst.

12. A process according to claim 10, wherein the reaction of said hydroxyalkyl triazolidine-3,5-dione with said alcohol is effected in the presence of a catalyst.

13. A process according to claim 10, wherein hydroxyalkyl triazolidine-3,5-diones are isolated following reaction of the triazolidine-3,5-dione with said aldehyde or ketone and said hydroxyalkyl triazolidine-3,5-dione is thereafter reacted with said alcohol.

14. A process according to claim 10, wherein the so-formed hydroxyalkyl triazolidine-3,5-diones are reacted with said alcohol without being isolated.

15. A process according to claim 10, wherein said triazolidine-3,5-dione is reacted simultaneously with an aldehyde or ketone of said formula and with an alcohol of said formula.

16. A process according to claim 10, wherein the process is carried out at a temperature of 10° to 200° C.

17. A process according to claim 16, wherein the process is carried out in the presence of a catalyst.

18. A process according to claim 16, wherein the process is carried out in the presence of a solvent.

19. A process according to claim 10, wherein the reaction of said hydroxyalkyl triazolidine-3,5-dione with said alcohol is effected at a temperature of 30° to 200° C.

20. A process according to claim 19, wherein the process is carried out in the presence of a mineral acid as catalyst.

* * * * *